United States Patent [19]
Dubief et al.

[11] Patent Number: 6,007,800
[45] Date of Patent: Dec. 28, 1999

[54] COMPOSITION CONTAINING POLYSILOXANE BACKBONE GRAFTED BY NON-SILICONE ORGANIC MONOMERS AND LIQUID HYDROCARBON

[75] Inventors: Claude Dubief, Le Chesnay; Christine Dupuis; Daniele Cauwet-Martin, both of Paris, all of France

[73] Assignee: L'Oreal, France

[21] Appl. No.: 08/983,334

[22] PCT Filed: Sep. 16, 1996

[86] PCT No.: PCT/FR96/01434

§ 371 Date: Dec. 30, 1997

§ 102(e) Date: Dec. 30, 1997

[87] PCT Pub. No.: WO97/12585

PCT Pub. Date: Apr. 10, 1997

[30] Foreign Application Priority Data

Sep. 29, 1995 [FR] France ................................. 95 11480

[51] Int. Cl.⁶ ........................................................ A61K 7/06
[52] U.S. Cl. ................. 424/70.1; 424/70.12; 424/70.15; 424/70.17
[58] Field of Search ............................. 424/70.12, 70.15, 424/70.17, 70.1

[56] References Cited

U.S. PATENT DOCUMENTS

| | | | |
|---|---|---|---|
| 5,362,485 | 11/1994 | Hayama et al. | 424/70 |
| 5,565,193 | 10/1996 | Midha | 424/70.12 |
| 5,589,162 | 12/1996 | Muraoka | 424/70.12 |
| 5,609,856 | 3/1997 | Dubief | 424/70.1 |
| 5,658,557 | 8/1997 | Bolich | 424/70.12 |

FOREIGN PATENT DOCUMENTS

| | | |
|---|---|---|
| 0 388 582 A2 | 9/1990 | European Pat. Off. . |
| 0 388 582 A3 | 9/1990 | European Pat. Off. . |
| 0 636 361 | 2/1995 | European Pat. Off. . |
| WO 93/23446 | 11/1993 | WIPO . |
| WO 95/03776 | 2/1995 | WIPO . |
| WO 95/04518 | 2/1995 | WIPO . |
| WO 95/05800 | 3/1995 | WIPO . |
| WO 95/06078 | 3/1995 | WIPO . |

OTHER PUBLICATIONS

English Language Derwent Abstract of EP 0 636 361.

*Primary Examiner*—Thurman K. Page
*Assistant Examiner*—Lakshmi Channavajjala
*Attorney, Agent, or Firm*—Finnegan, Henderson, Farabow, Garrett & Dunner

[57] ABSTRACT

The present invention relates to a composition for the treatment of keratinous material, in particular human hair, comprising, in a cosmetically or dermatologically acceptable medium, at least one grafted silicone polymer, containing a polysiloxane skeleton grafted with non-silicone organic monomers and at least one hydrocarbon which is liquid at room temperature, the hydrocarbon chain of which has from 11 to 26 linear or branched, cyclic or acyclic carbon atoms, as well as its applications.

The compositions according to the invention are used in particular as rinse-out products or as leave-in products, in particular for the washing, care and conditioning of the hair, for maintaining the hairstyle or for shaping the hairstyle.

36 Claims, No Drawings

COMPOSITION CONTAINING POLYSILOXANE BACKBONE GRAFTED BY NON-SILICONE ORGANIC MONOMERS AND LIQUID HYDROCARBON

The present invention relates to a cosmetic or dermatological composition for the treatment of keratinous material, in particular human hair, comprising at least one grafted silicone polymer, containing a polysiloxane skeleton grafted with non-silicone organic monomers and at least one hydrocarbon which is liquid at room temperature, the hydrocarbon chain of which has from 11 to 26 carbon atoms, as well as its applications, in particular in the field of hair cosmetics.

The polymers of the type such as a polymer containing a polysiloxane skeleton grafted with non-silicone organic monomers are known for their styling properties. However, these polymers lead to unsatisfatory cosmetic properties when they are applied.

The Applicant has found, surprisingly, that by combining linear or branched, cyclic or acyclic hydrocarbons that are liquid at room temperature, in which the hydrocarbon chain has from 11 to 26 carbon atoms, with these types of polymer, the cosmetic properties are improved, in particular the disentangling of the hair and the softness to the touch while at the same time retaining the styling properties of these polymers.

The composition according to the invention is thus essentially characterized in that it contains, in a cosmetically or dermatologically acceptable medium, at least one grafted silicone polymer, containing a polysiloxane skeleton grafted with non-silicone organic monomers and at least one hydrocarbon which is liquid at room temperature, the hydrocarbon chain of which has from 11 to 26 linear or branched, cyclic or acyclic carbon atoms.

In the following text, in accordance with that which is generally accepted, the term silicone polymer is understood to denote any organosilicon polymer or oligomer with a branched or crosslinked, linear or cyclic structure, of variable molecular weight, obtained by polymerization and/or polycondensation of suitably functionalized silanes, and consisting essentially of a repetition of main units in which the silicon atoms are linked together by oxygen atoms (siloxane linkage $\equiv$Si—O—Si$\equiv$), optionally substituted hydrocarbon radicals being linked directly via a carbon atom to the said silicon atoms. The most common hydrocarbon radicals are alkyl radicals, notably $C_1$–$C_{10}$ alkyl radicals and in particular methyl, fluoroalkyl radicals, aryl radicals and in particular phenyl, and alkenyl radicals and in particular vinyl; other types of radicals which may be linked, either directly or via a hydrocarbon radical, to the siloxane chain are, notably, hydrogen, halogens and in particular chlorine, bromine or fluorine, thiols, alkoxy radicals, polyoxyalkylene (or polyether) radicals and in particular polyoxyethylene and/or polyoxypropylene, hydroxyl or hydroxyalkyl radicals, substituted or unsubstituted amine groups, amide groups, acyloxy or acyloxyalkyl radicals, hydroxyalkylamino or aminoalkyl radicals, quaternary ammonium groups, amphoteric or betaine groups and anionic groups such as carboxylates, thioglycolates, sulphosuccinates, thiosulphates, phosphates and sulphates, this list not, of course, being limiting in any way (so-called "organomodified" silicones).

According to the present invention, the silicone polymer or polymers which must be used are those which comprise a main chain of silicone (or polysiloxane ($\equiv$Si—O—)$_n$) on which is grafted, inside the said chain as well as optionally on at least one of its ends, at least one organic group containing no silicone.

These silicone polymers may be existing commercial products or may be obtained according to any means known to those skilled in the art, in particular by reaction between (i) a starting silicone correctly functionalized on one or more of these silicon atoms and (ii) a non-silicone organic compound which is itself correctly functionalized with a function which is capable of reacting with the functional group or groups carried by the said silicone, forming a covalent bond; a standard example of such a reaction is the hydrosilylation reaction between $\equiv$Si—H groups and $CH_2$=CH— vinyl groups, or alternatively the reaction between —SH thiofunctional groups and these same vinyl groups.

Examples of silicone polymers which are suitable for carrying out the present invention, as well as their particular mode of preparation, are described in particular in patent applications EP-A-0,582,152, WO 93/23009 and WO 95/03776, the teachings of which are included in their entirety in the present description by way of non-limiting references.

According to a particularly preferred embodiment of the present invention, the silicone polymer used comprises the result of the radical copolymerization between, on the one hand, at least one non-silicone anionic organic monomer having ethylenic unsaturation and/or a non-silicone hydrophobic organic monomer having ethylenic unsaturation, and, on the other hand, a silicone having in its chain at least one functional group capable of reacting with the said ethylenic unsaturations of the said non-silicone monomers, forming a covalent bond, in particular thiofunctional groups.

According to the present invention, the said anionic monomers containing ethylenic unsaturation are preferably chosen, alone or as mixtures, from linear or branched, unsaturated carboxylic acids optionally partially or totally neutralized in the form of a salt, it being possible for this or these unsaturated carboxylic acid or acids more particularly to be acrylic acid, methacrylic acid, maleic acid, maleic anhydride, itaconic acid, fumaric acid and crotonic acid. The suitable salts are, in particular, alkali metal, alkaline-earth metal and ammonium salts. Similarly, it will be noted that in the final grafted silicone polymer, the organic group of anionic nature which comprises the result of the radical (homo)polymerization of at least one anionic monomer of unsaturated carboxylic acid type may be, after reaction, post-neutralized with a base (sodium hydroxide, aqueous ammonia etc.) to bring it into the form of a salt.

According to the present invention, the hydrophobic monomers containing ethylenic unsaturation are preferably chosen, alone or as mixtures, from alkanol esters of acrylic acid and/or alkanol esters of methacrylic acid. The alkanols are preferably $C_1$–$C_{18}$ and more particularly $C_1$–$C_{12}$. The preferred monomers are chosen from the group consisting of isooctyl (meth)acrylate, isononyl (meth)acrylate, 2-ethylhexyl (meth)acrylate, lauryl (meth)acrylate, isopentyl (meth)acrylate, n-butyl (meth)acrylate, isobutyl (meth)acrylate, methyl (meth)acrylate, tert-butyl (meth)acrylate, tridecyl(meth)acrylate and stearyl (meth)acrylate, or mixtures thereof.

One family of grafted silicone polymers which is particularly suitable for carrying out the present invention consists of silicone polymers containing in their structure the unit of formula (I) below:

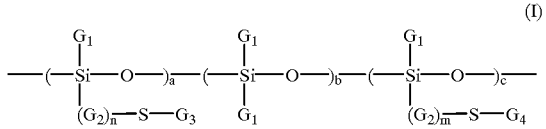

in which the radicals $G_1$, which may be identical or different, represent hydrogen or a $C_1$–$C_{10}$ alkyl radical or alternatively a phenyl radical; the radicals $G_2$, which may be identical or different, represent a $C_1$–$C_{10}$ alkylene group; $G_3$ represents a polymer residue resulting from the (homo)polymerization of at least one anionic monomer containing ethylenic unsaturation; $G_4$ represents a polymer residue resulting from the (homo)polymerization of at least one hydrophobic monomer containing ethylenic unsaturation; m and n are equal to 0 or 1; a is an integer ranging from 0 to 50; b is an integer which may be between 10 and 350, c is an integer ranging from 0 to 50; with the proviso that one of the parameters a and c is other than 0.

Preferably, the unit of formula (I) above has at least one, and more preferably all, of the following characteristics:

the radicals $G_1$ denote an alkyl radical, preferably the methyl radical;

n is non-zero, and the radicals $G_2$ represent a divalent $C_1$–$C_3$ radical, preferably a propylene radical;

$G_3$ represents a polymer radical resulting from the (homo) polymerization of at least one monomer of the carboxylic acid type containing ethylenic unsaturation, preferably acrylic acid and/or methacrylic acid;

$G_4$ represents a polymer radical resulting from the (homo) polymerization of at least one monomer of the ($C_1$–$C_{10}$)alkyl (meth)acrylate type, preferably isobutyl or methyl (meth)acrylate.

Examples of silicone polymers corresponding to formula (I) are, in particular, polydimethylsiloxanes (PDMS) on which are grafted, via a thiopropylene-type linking chain, mixed polymer units of the poly(meth)acrylic acid type and of the polymethyl (meth)acrylate type.

Other examples of silicone polymers corresponding to formula (I) are polydimethylsiloxanes (PDMS) on which are grafted, via a thiopropylene-type linking chain, polymer units of the polyisobutyl (meth)acrylate type.

Preferably, the number-average molecular mass of the silicone polymers of the invention ranges approximately from 10,000 to 1,000,000 and even more preferably approximately from 10,000 to 100,000.

The grafted silicone polymer is preferably used in an amount ranging from 0.01 to 20% by weight relative to the total weight of the composition. More preferably, this amount ranges from 0.1 to 15% by weight and even more preferably, from 0.5 to 10% by weight.

The linear or branched, cyclic or acyclic hydrocarbons that are liquid at room temperature, in accordance with the invention, are preferably chosen from isododecane ($C_{12}$), isohexadecane ($C_{16}$) and isomers thereof such as 2, 2, 4, 4, 6, 6-heptamethylnonane ($C_{16}$), isoeicosane ($C_{20}$) and isotetracosane ($C_{24}$) and isomers thereof. Isododecane ($C_{12}$) or one of the isomers thereof is used more particularly.

The liquid hydrocarbons in accordance with the invention are preferably used in an amount ranging from 0.01 to 10% by weight relative to the total weight of the composition. Even more preferably, this amount ranges from 0.5 to 5% by weight.

The cosmetically or dermatologically acceptable medium preferably consists of water or of a mixture of water and cosmetically acceptable solvents such as monoalcohols, polyalcohols, glycol ethers or fatty acid esters, which may be used alone or as a mixture.

Mention may be made more particularly of lower alcohols such as ethanol and isopropanol, polyalcohols such as diethylene glycol, glycol ethers, and alkyl ethers of glycol or of diethylene glycol.

The grafted silicone polymers according to the invention may be dissolved in the said cosmetically acceptable medium or used in the form of an aqueous dispersion of particles.

The composition of the invention may also contain at least one additive chosen from thickeners, fatty acid esters, fatty acid esters of glycerol, silicones, surfactants, fragrances, preserving agents, sunscreens, proteins, vitamins, polymers, plant, animal, mineral or synthetic oils and any other additive conventionally used in the cosmetics field.

These additives are present in the composition according to the invention in proportions which may range from 0 to 20% by weight relative to the total weight of the composition. The precise amount of each additive depends on its nature and is readily determined by a person skilled in the art.

Obviously, a person skilled in the art will take care to select the optional compound or compounds to be added to the composition according to the invention such that the advantageous properties intrinsically associated with the composition in accordance with the invention are not, or are substantially not, adversely affected by the addition envisaged.

The compositions according to the invention may be in the form of a gel, a milk, a cream, a more or less thickened lotion or a foam.

These compositions are more particularly hair-setting lotions, blow-drying lotions, fixing compositions (lacquers) and styling compositions. The lotions may be packaged in various forms, in particular in vaporizers, pump-dispenser bottles or in aerosol cans, in order to ensure application of the composition in vaporized form or in the form of a foam. Such packaging forms are indicated, for example, when it is desired to obtain a spray, a lacquer or a foam for fixing or treating the hair.

The compositions may also be shampoos, rinse-out or leave-in compositions to be applied before or after shampooing, dying, bleaching, permanent-waving or straightening of the hair.

When the composition according to the invention is packaged in aerosol form in order to obtain an aerosol foam or lacquer, it comprises at least one propellant which may be chosen from volatile hydrocarbons such as n-butane, propane, isobutane, pentane, a chlorinated and/or fluorinated hydrocarbon, and mixtures thereof. Carbon dioxide, nitrous oxide, dimethyl ether, nitrogen, compressed air and mixtures thereof may also be used as propellants.

The subject of the invention is also a non-therapeutic process for the treatment of keratinous material, such as the hair, which consists in applying to the hair a composition as defined above, optionally followed by rinsing with water.

The invention will now be illustrated more fully with the aid of the examples which follow, which should not be considered as limiting it to the embodiments described.

EXAMPLES

Example 1

Styling Spray In A Pump-Dispenser Bottle

| | |
|---|---|
| grafted silicone polymer of formula (I) of polymethyl/methylsiloxane structure containing 3-propylthio polymethacrylic acid groups and 3-propylthio polymethyl methacrylate groups | 6 g AM |
| isododecane ($C_{12}$) | 3 g |
| aminomethylpropanol, 100% neutralization of the said silicone polymer qs | |
| ethanol qs | 100 g |

Example 2

Aerosol Styling Spray

| | |
|---|---|
| grafted silicone polymer of formula (I) of polymethyl/methylsiloxane structure containing 3-propylthio polymethacrylic acid groups and 3-propylthio polymethyl methacrylate groups | 5 g AM |
| vinyl acetate/crotonic acid/vinyl 4-tert-butylbenzoate copolymer (65/10/25) neutralized as described and prepared in patent FR 2,697,160 | 2.5 g AM |
| isododecane ($C_{12}$) sold under the name Permethyl 99A by the company Presperse Inc. | 3 g |
| aminomethylpropanol, 100% neutralization of the said grafted silicone polymer and of the copolymer qs | |
| ethanol qs | 100 g |

Pressurization Plan

| | |
|---|---|
| above composition | 80 g |
| isobutane | 15 g |
| 1,1-difluoroethane | 5 g |

Example 3

Styling Gel

| | |
|---|---|
| grafted silicone polymer of formula (I) of polymethyl/methylsiloxane structure containing 3-propylthio polymethacrylic acid groups and 3-propylthio polymethyl methacrylate groups | 4 g AM |
| poly(acrylic acid) polymer sold under the name Synthalen K by the company 3V | 0.5 g AM |
| vinylpyrrolidone/vinyl acetate copolymer sold under the name PVP/VA 735 by the company ISP | 1 g AM |
| 2,2,4,4,6,6-heptamethylnonane ($C_{16}$) sold under the name Arlanol HD by ICI | 3 g |
| aminomethylpropanol, 100% neutralization of the said silicone polymer and of the acrylic polymer qs | |
| ethanol | 20 g |
| demineralized water qs | 100 g |

Example 4

Shampoo

| | |
|---|---|
| grafted silicone polymer of formula (I) of polymethyl/methylsiloxane structure containing 3-propylthio polyisobutyl methacrylate groups | 1 g AM |
| isoeicosane ($C_{20}$) | 2 g |
| sodium lauryl ether sulphate ($C_{12}/C_{14}$; 70/30) containing 22 mol of ethylene oxide, as an aqueous solution sold under the name Empicol ESB 31/F by the company Albright and Wilson | 15 g |
| cocoylbetaine | 3 g |
| sodium cetostearyl sulphate ($C_{16}/C_{18}$; 50/50) sold under the name Laneth by Henkel | 0.8 g |
| 1-(hexadecyloxy)-2-octadecanol/cetyl alcohol mixture (47/53) | 2.5 g |
| coconut acid monoisopropanolamide | 2 g |
| fragrance, preserving agent qs | |
| water qs pH adjusted to 5.5 with HCl | 100 g |

Example 5

Conditioner

| | |
|---|---|
| grafted silicone polymer of formula (I) of polymethyl/methylsiloxane structure containing 3-propylthio polyisobutyl methacrylate groups | 1 g AM |
| 2,2,4,4,6,6-heptamethylnonane ($C_{16}$) sold under the name Arlanol HD by ICI | 2 g |
| acrylamide/2-acrylamidomethylpropanesulphonic acid copolymer in the form of the sodium salt, as a 40% inverted emulsion in an isoparaffin/water mixture, such as the product described in Example 1 of document EP-A-503,853 | 1 g AM |
| α,ω-dihydroxylated polydimethylsiloxane/cylcotetra- and cylcopentadimethylsiloxane mixture (56/44) (14/86) sold under the name QCF2-1671 Fluid by Dow Corning | 10 g |
| fragrance, preserving agent qs | |
| water qs pH adjusted to 6 with NaOH | 100 g |

We claim:

1. A cosmetic or dermatological composition comprising, in a cosmetically or dermatologically acceptable medium,
   (a) at least one grafted silicone polymer containing a polysiloxane skeleton grafted with at least one non-silicone organic monomer and
   (b) at least one hydrocarbon wherein said hydrocarbon is liquid at room temperature and the chain of said hydrocarbon has from 11 to 26 linear or branched, cyclic or acyclic carbon atoms.

2. A cosmetic or dermatological composition according to claim 1, wherein said at least one grafted silicone polymer comprises a polysiloxane skeleton on which is grafted, inside said skeleton as well as, optionally, on at least one of its ends, said at least one non-silicone organic monomer.

3. A cosmetic or dermatological composition according to claim 2, wherein said at least one grafted silicone polymer is obtained by radical copolymerization between
   (a) at least one non-silicone organic monomer having ethylenic unsaturation selected from anionic and hydrophobic monomers, and
   (b) at least one polysiloxane having, in its skeleton, at least one functional group capable of reacting with said ethylenic unsaturation of said at least one non-silicone organic monomer.

4. A cosmetic or dermatological composition according to claim 3, wherein said polysiloxane has several functional groups capable of reacting with said ethylenic unsaturation of said at least one non-silicone organic monomer.

5. A cosmetic or dermatological composition according to claim 3, wherein said at least one non-silicone anionic organic monomer is selected from linear and branched unsaturated carboxylic acids, optionally partially and totally neutralized in the form of a salt.

6. A cosmetic or dermatological composition according to claim 5, wherein said at least one non-silicone anionic organic monomer is selected from acrylic acid, methacrylic acid, maleic acid, maleic anhydride, itaconic acid, fumaric acid, crotonic acid, alkali-metal salts of the above acids, alkaline-earth metal salts of the above acids and ammonium salts of the above acids.

7. A cosmetic or dermatological composition according to claim 3, wherein said at least one non-silicone hydrophobic organic monomer is selected from acrylic acid esters of an alkanol and methacrylic acid esters of an alkanol.

8. A cosmetic or dermatological composition according to claim 7, wherein said alkanol is $C_1$–$C_{18}$.

9. A cosmetic or dermatological composition according to claim 8, wherein said alkanol is $C_1$–$C_{12}$.

10. A cosmetic or dermatological composition according to claim 3, wherein said at least one non-silicone hydrophobic organic monomer is selected from isooctyl (meth) acrylate, isononyl (meth)acrylate, 2-ethylhexy (meth) acrylate, lauryl (meth)acrylate, isopentyl (meth)acrylate, n-butyl (meth)acrylate, isobutyl (meth)acrylate, methyl (meth)acrylate, tert-butyl (meth)acrylate, tridecyl (meth) acrylate and stearyl (meth)acrylate.

11. A cosmetic or dermatological composition according to claim 1, wherein said at least one grafted silicone polymer comprises, on the main polysiloxane skeleton, at least one non-silicone organic group of anionic nature obtained by radical (homo)polymerization of at least one non-silicone anionic monomer of unsaturated carboxylic acid type, partially or totally neutralized in the form of a salt.

12. A cosmetic or dermatological composition according to claim 1, wherein said at least one grafted silicone polymer is selected from silicone polymers containing in their structure the unit of formula (I).

$$—(-\underset{(G_2)_{\overline{n}}-S-G_3}{\overset{G_1}{\underset{|}{Si}}}-O-)_a-(-\underset{G_1}{\overset{G_1}{\underset{|}{Si}}}-O-)_b-(-\underset{(G_2)_{\overline{m}}-S-G_4}{\overset{G_1}{\underset{|}{Si}}}-O-)_c- \quad (I)$$

in which:
the radicals $G_1$ each independently represent hydrogen or a $C_1$–$C_{10}$ alkyl radical or a phenyl radical;
the radicals $G_2$ each independently represent a divalent $C_1$–$C_{10}$ alkylene group;
$G_3$ represents a polymer residue resulting from the (homo)polymerization of at least one anionic monomer containing ethylenic unsaturation;
$G_4$ represents a polymer residue resulting from the (homo)polymerization of at least one hydrophobic monomer containing
ethylenic unsaturation;
m and n are equal to 0 or 1;
a is an integer ranging from 0 to 50;
b is an integer ranging from 10 to 350;
c is an integer ranging from 0 to 50;
with the proviso that one of a and c is not 0.

13. A cosmetic or dermatological composition according to claim 12, wherein said unit of formula (I) has at least one of the following characteristics:
the radicals $G_1$ denote a $C_1$–$C_{10}$ alkyl radical;
n is non-zero and the radicals $G_2$ represent a divalent $C_1$–$C_3$ radical;
$G_3$ represents a polymeric residue resulting from the (homo)polymerization of at least one carboxylic acid monomer containing ethylenic unsaturation; and
$G_4$ represents a polymeric residue resulting from the (homo)polymerization of at least one $C_1$–$C_{10}$ alkyl (meth)acrylate monomer.

14. A cosmetic or dermatological composition according to claim 12, wherein said unit of formula (I) simultaneously has the following characteristics:
the radicals $G_1$ denote a methyl radical;
n is non-zero and the radicals $G_2$ represent a propylene radical;
$G_3$ represents a polymeric residue resulting from the (homo)polymerization of at least one monomer selected from acrylic acid and methacrylic acid;
$G_4$ represents a polymeric radical resulting from the (homo)polymerization of at least one monomer selected from isobutyl and methyl (meth)acrylate monomers.

15. A cosmetic or dermatological composition according to claim 1, wherein the number-average molecular mass of said at least one grafted silicone polymer ranges from 10,000 to 1,000,000.

16. A cosmetic or dermatological composition according to claim 15, wherein said number-average molecular mass of said at least one grafted silicone polymer ranges from 10,000 to 100,000.

17. A cosmetic or dermatological composition according to claim 1, wherein said at least one grafted silicone polymer is present in a concentration ranging from 0.01 to 20% by weight relative to the total weight of said composition.

18. A cosmetic or dermatological composition according to claim 17, wherein said at least one grafted silicone polymer is present in a concentration ranging from 0.1 to 15% by weight relative to the total weight of said composition.

19. A cosmetic or dermatological composition according to claim 18, wherein said at least one grafted silicone polymer is present in a concentration ranging from 0.5 to 10% by weight relative to the total weight of said composition.

20. A cosmetic or dermatological composition according to claim 1, wherein said at least one hydrocarbon is selected from isododecane ($C_{12}$), isohexadecane ($C_{16}$), isoeicosane ($C_{20}$), isotetracosane ($C_{24}$) and isomers thereof.

21. A cosmetic or dermatological composition according to claim 20, wherein said at least one hydrocarbon is selected from isododecane ($C_{12}$) and isomers thereof.

22. A cosmetic or dermatological composition according to claim 1, wherein said at least one hydrocarbon is present in a concentration ranging from 0.01 to 10% by weight relative to the total weight of said composition.

23. A cosmetic or dermatological composition according to claim 22, wherein said at least one hydrocarbon is present in a concentration ranging from 0.5 to 5% by weight relative to the total weight of said composition.

24. A cosmetic or dermatological composition according to claim 1, wherein said composition further comprises at least one additive selected from thickeners, fatty acid esters, fatty acid esters of glycerol, silicones, surfactants, fragrances, preserving agents, sunscreens, proteins, vitamins, different polymers, plant, animal, mineral and synthetic oils and any other suitable cosmetic additive.

25. A cosmetic or dermatological composition according to claim 1, wherein said cosmetically or dermatologically acceptable medium comprises water or a mixture of water and at least one cosmetically acceptable solvent.

26. A cosmetic or dermatological composition according to claim 25, wherein said at least one cosmetically acceptable solvent is selected from monoalcohols, polyalcohols, glycol ethers and fatty acid esters.

27. A cosmetic or dermatological composition according to claim 1, wherein said at least one grafted silicone polymer is dissolved in the cosmetically or dermatologically acceptable medium or is in the form of an aqueous dispersion of particles.

28. A cosmetic or dermatological composition according to claim 1 wherein said composition is a treatment composition for a keratin substance.

29. A cosmetic or dermatological composition according to claim 28, wherein said keratin substance is human hair.

30. A cosmetic or dermatological composition according to claim 1, wherein said composition is in the form of a gel, a milk, a cream, a thickened lotion or a foam.

31. A cosmetic or dermatological composition according to claim 1, wherein said composition is a styling product.

32. A cosmetic or dermatological composition according to claim 1, wherein said composition is a hair product to be applied before or after shampooing, dyeing, bleaching, permanent-waving or straightening the hair.

33. A cosmetic or dermatological composition according to claim 32, wherein said hair product is selected from shampoos and rinse-out and leave-in hair products.

34. A cosmetic or dermatological composition according to claim 1, wherein said composition is packaged in the form of a vaporizer, a pump-dispenser bottle or in an aerosol container.

35. A non-therapeutic process for treating a keratin substance comprising applying a composition according to claim 1 to said keratin substance, and then optionally rinsing with water.

36. A non-therapeutic process according to claim 35, wherein said keratin substance is human hair.

* * * * *

UNITED STATES PATENT AND TRADEMARK OFFICE
CERTIFICATE OF CORRECTION

PATENT NO.: 6,007,800

DATED: December 28, 1999

INVENTOR(S): Claude Dubief; Christine Dupuis; Daniele Cauwet-Martin

It is certified that an error appears in the above-identified patent and that said Letters Patent is hereby corrected as shown below:

In claim 3, col. 6, line 57, "claim 2" should read --claim 1--.

Signed and Sealed this

Twelfth Day of December, 2000

Attest:

Q. TODD DICKINSON

*Attesting Officer*     *Director of Patents and Trademarks*